US00PP25160P3

(12) United States Plant Patent
Schoone

(10) Patent No.: US PP25,160 P3
(45) Date of Patent: Dec. 9, 2014

(54) ***PHALAENOPSIS* ORCHID PLANT NAMED 'GRISSINI'**

(50) Latin Name: ***Phalaenopsis* hybrid**
Varietal Denomination: Grissini

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 14 days.

(21) Appl. No.: 13/986,267

(22) Filed: Apr. 18, 2013

(65) Prior Publication Data

US 2013/0291240 P1 Oct. 31, 2013

Related U.S. Application Data

(60) Provisional application No. 61/638,210, filed on Apr. 25, 2012.

(30) Foreign Application Priority Data

Apr. 26, 2012 (NL) ..... PBR OPS893

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP; Sunit Talapatra

(57) ABSTRACT

A new and distinct *Phalaenopsis* plant named 'Grissini' particularly characterized by flowers which are green/yellow with orange/red spots with a purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Grissini'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Grissini'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Grissini' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Grissini' originated from a cross made by the inventor in 1999 in Strengweg, Heemskerk, The Netherlands. The female or seed parent is the *Phalaenopsis* cultivar designated 'Sunrise Delight', unpatented. The male or pollen parent is the *Phalaenopsis* cultivar designated 'Timothy Christopher', unpatented. The new *Phalaenopsis* 'Grissini' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Grissini', which in combination distinguish this *Phalaenopsis* as a new and distinct cultivar:

1. flowers which are green/yellow with orange/red spots and a purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Grissini', the female parent 'Sunrise Delight' has yellow/orange flowers with a red/orange labellum and the male parent 'Timothy Christopher' has white colored flowers, whereas the flowers of 'Grissini' are green/yellow with orange/red spots and a purple labellum.

Presently, there is no other commercial cultivar to which 'Grissini' can be meaningfully compared.

BRIEF DESCRIPTION OF THE PHOTOGRAPHS

The accompanying photographs illustrate the overall appearance of the new *Phalaenopsis* 'Grissini' showing the colors as true as is reasonably possible with colored reproductions of this type. Colors in the photographs may differ slightly from the color values cited in the detailed botanical description, which accurately describe the color of 'Grissini'.

DETAILED BOTANICAL DESCRIPTION

Figure 1:
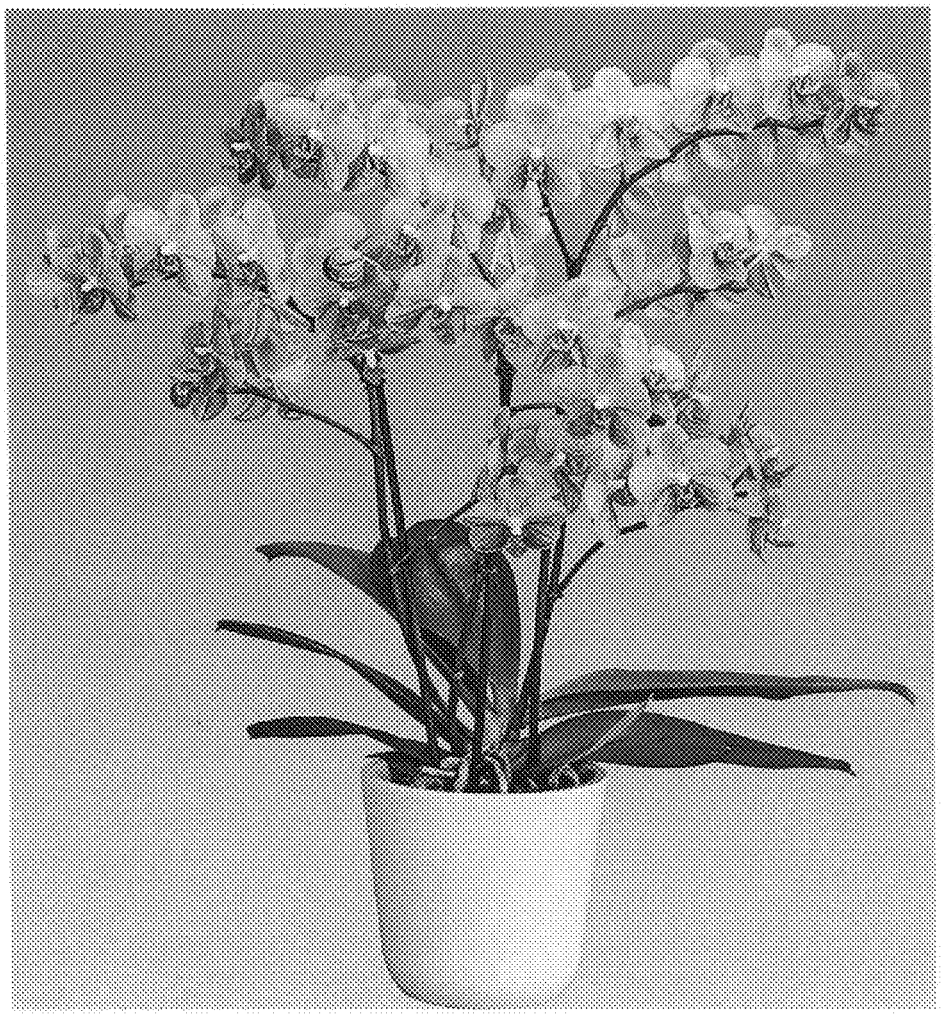
FIG. 1 shows a side view perspective of a typical flowering plant of 'Grissini' in a 12 cm pot, at 16 months of age.

The new *Phalaenopsis* cultivar 'Grissini' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Grissini' as grown in a greenhouse in Strengweg, Heemskerk, The Netherlands, under conditions which closely approximate those generally used in commercial practice. Initially, the ideal temperature to grow plants of 'Grissini' is 27° C. during the day and at night. Then, during the flowering phase of 'Grissini', the ideal growing temperature is 20-22° C. during the day and 18° C. at night. Light levels for growing 'Grissini' are a minimum of 5,000 lux and a maximum of 10,000 lux. A balanced fertilizer with level of 200 ppm N, 87 ppm P, 168 ppm K is applied. Duration of growth of 'Grissini' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Grissini' plants described is 12 months after potting.

Classification:

*Botanical.*—*Phalaenopsis* hybrid.

Parentage:

*Female or seed parent.*—*Phalaenopsis* cultivar designated 'Sunrise Delight', unpatented.

*Male or pollen parent.*—*Phalaenopsis* cultivar designated 'Timothy Christopher', unpatented.

Propagation:

*Type.*—Tissue culture.

*Rooting habit and description.*—Fleshy; approximately 3 mm-6 mm wide and green in color (RHS 143 C and RHS 191C); freely branching. It takes 12 weeks for plants growing in tissue culture to initiate roots.

Plant:

*Size at maturity.*—Height: about 57 cm. Spread: about 53 cm.

*Growth habit.*—Small; dark-green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture* (*upper* & *underside*).—Smooth and leathery.

*Mature leaf length.*—About 13 to 25 cm.

*Mature leaf width.*—About 6 and 10 cm.

*Mature leaf thickness.*—About 1.5 mm.

*Mature leaf color.*—Upper side: green (RHS 137B); the edges are RHS 138B. Under side: green (RHS 144A); the edges are RHS 138B.

*Leaf base.*—Acute.

*Margin.*—Entire.

*Venation.*—Pattern: parallel. Color of midvein: upper side: some grey/purple (RHS 183B) and some green (RHS 143A); under side: some grey/purple (RHS 183C) and some green (RHS 144B).

Raceme:

*Quantity per plant.*—About 1 to 3.

*Number of flowers per raceme.*—About 10 to 15.

*Length.*—About 45 to 51 cm.

*Diameter.*—About 3 mm to 6 mm.

*Strength.*—Strong.

*Aspect.*—Upright.

*Texture.*—Glabrous and smooth.

*Color.*—In the top green (RHS 144A) and on the bottom green (RHS 146A).

*Internode.*—Length: about 33 to 45 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 22 mm. Diameter (at midpoint): about 17 mm. Shape: egg-shaped. Color: yellow/green (RHS N144A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—Very light fragrance.

Figure 2:
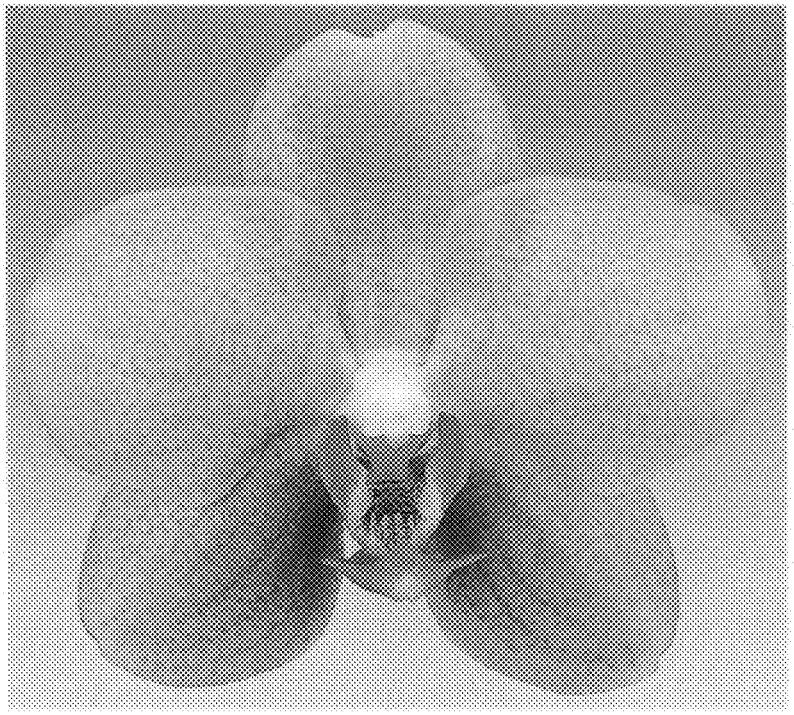
FIG. 2 shows a close-up view of the typical buds and flowers of 'Grissini'.
Figure 3:
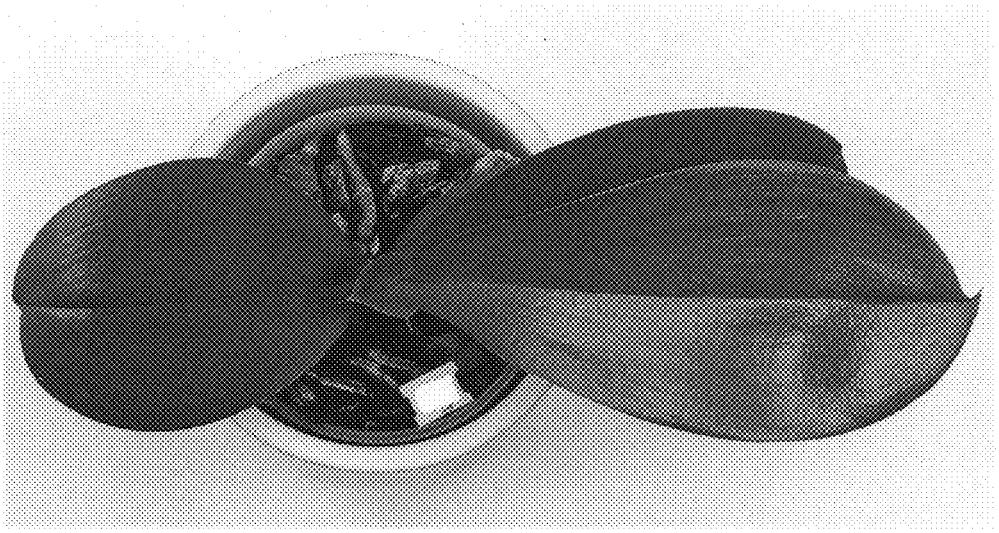
FIG. 3 shows a close-up view of the typical leaves of 'Grissini'.

*Flower*.—Rate of opening: Flowers fully opened about 2 to 3 days after petal and sepal separation. Orientation at opening: slanted upward and outward. Shape: see FIG. 2. Size: Height: about 40 mm to 65 mm. Diameter: about 52 mm to 68 mm. Depth of tube: about 5 mm.

*Petals*.—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate, little triangular and weakly cupped. Apex: oval. Margin: entire and weakly undulate. Base: broadly ovate. Length: about 33 mm. Width: about 32 mm. Texture: Upper surface: smooth and satiny. Under surface: smooth and satiny. Color (when fully opened): upper side: green/yellow (RHS 1 B) on the top, with some orange/red spots (RHS 31B). Close to the center red/purple (RHS 68B). Under side: green/yellow (RHS 1C), the midvein is yellow/green (RHS 154A). Close to the center red purple (RHS 68B). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: lateral lobes: oval. Mid lobe: round corners. Length: about 18 mm. Width (not flattened): about 15 mm. Texture: Upper and under surface: smooth and satiny. Color (when fully opened): Mid lobe: upper surface: at the top purple (RHS N78B), in the middle grey/orange (RHS N163A) and at the base yellow/orange (RHS 17B). Under surface: on the top purple (RHS N78B) which runs into RHS N78D. In the center some white (RHS NN155C) and on the outer edges of the center some yellow/orange (RHS 17B). At the base some grey/orange (RHS N163B). Lateral lobes: upper surface: at the top and on the lower edge some purple (RHS N78A), after that some white (RHS NN155C) with red/purple spots (RHS 60A). At the base some yellow (RHS 9B). Under surface: At the top and on the edges puple (RHS N78A). At the base some white (RHS NN155B). Chirri: very small (about 1 mm); color: RHS N78A. Pestle (Callosities): Length: about 6 mm. Width (not flattened): about 4 mm. Color: yellow (RHS 13B) with red/purple spots (RHS 60A).

*Sepals*.—Arrangement: Outer whorl comprises 3 sepals. Overall shape: elliptical and weakly cupped. Margin: entire and weakly undulate. Length: about 31 mm. Width: about 27 mm. Apex: dorsal: oval with a notch; lateral: oval with sometimes a small notch. Texture: Upper and under surface: smooth and satiny. Color (when fully opened): upper surface: yellow/green (RHS 1B) with orange/red spots (RHS 34C). At the base some red/purple (RHS 68B). At the base of the lateral sepals also some darker spots (RHS 59C) and a little white stripe (RHS NN155B). Under surface: yellow/green (RHS 1B). At the base the mid vein is red/purple (RHS 62D) and at the top yellow/green (RHS 150A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 5 mm. Color: white (RHS NN155B) and purple (RHS 68D).

*Pollinia*.—Quantity: two. Diameter: about 1 mm. Color: orange/yellow (RHS 23A).

*Ovary*.—Length: about 3 mm. Diameter: about 2 mm. Color: white (RHS NN155B).

*Pedicel*.—Length: about 23 to 45 mm. Diameter: about 3 mm. Texture: glabrous and smooth. Color: yellow/green (RHS 150B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Grissini', as illustrated and described herein.

* * * * *